United States Patent [19]

Yoneyama et al.

[11] Patent Number: 4,481,819
[45] Date of Patent: Nov. 13, 1984

[54] METHOD AND APPARATUS FOR DETECTING METAL WIPE DAMAGES OF PLANE BEARING

[75] Inventors: Takao Yoneyama; Ichiya Satoh; Sanshiro Obara; Tomoaki Inoue; Tsuguaki Koga, all of Hitachi, Japan

[73] Assignee: Hitachi, Ltd., Tokyo, Japan

[21] Appl. No.: 465,183

[22] Filed: Feb. 9, 1983

Related U.S. Application Data

[63] Continuation of Ser. No. 195,106, Oct. 8, 1980, abandoned.

[30] Foreign Application Priority Data

Oct. 8, 1979 [JP] Japan .................................. 54-128918

[51] Int. Cl.³ .......................................... G01N 29/04
[52] U.S. Cl. ........................................ 73/593; 73/660
[58] Field of Search ................ 73/593, 660, 659; 374/153; 116/216

[56] References Cited

U.S. PATENT DOCUMENTS

| | | | |
|---|---|---|---|
| 2,114,029 | 4/1938 | Perry | 374/57 |
| 3,052,123 | 9/1962 | Gustafson | 116/216 |
| 3,842,663 | 10/1974 | Harting et al. | 73/593 |
| 4,007,630 | 2/1977 | Noda | 73/593 |
| 4,262,538 | 4/1981 | Otawara | 73/593 |

Primary Examiner—Anthony V. Ciarlante
Attorney, Agent, or Firm—Antonelli, Terry & Wands

[57] ABSTRACT

A method and apparatus for detecting metal wipe damages of plane bearings with the metal wipe generating an ultrasonic signal as an acoustic emission signal when it occurs. The ultrasonic signal has a periodic appearance therefore, the metal wipe damages, can be detected by monitoring the periodic nature of the ultrasonic signal. The ultrasonic signal is received by a transducer fixed to the plane bearing with the periodic nature of the received ultrasonic signal being computed by a processing unit so as to provide a output signal of the occurrence of a metal wipe when the received ultrasonic signal is periodic.

12 Claims, 7 Drawing Figures

METHOD AND APPARATUS FOR DETECTING METAL WIPE DAMAGES OF PLANE BEARING

This is a continuation of application Ser. No. 195,106, filed Oct. 8, 1980 now abandoned.

BACKGROUND OF THE INVENTION

This invention relates to a method and apparatus for detecting metal wipe damages of plane bearings which are used in rotary machines.

Burn-out of bearing metal leads to serious problems especially in large-sized steam turbine generators rotating at high speed. Therefore, it is highly desirable to detect, in plane bearings metal wipe damages caused by, for example axial vibration, rubbing when the generators are in operation.

In, for example, "Instrumentation Technology", September, 1977, pp 59-60, a popular detection method is proposed wherein a temperature of bearings is monitored; however, a disadvantage of this proposed method resides in the fact that the detection is effected only after an enlargement of the metal wipe. Accordingly, it is very difficult to detect the metal wipe damages in an initial stage before the rubbing occurs.

SUMMARY OF THE INVENTION

Accordingly, it is an object of this invention to provide a method and apparatus for detecting a occurrence of the metal wipe.

Another object of this invention is to provide a method and apparatus for detecting an enlarged state of the metal wipe damages.

The metal wipe which leads to the rubbing, etc. generates ultrasonic signal (as acoustic emission signal) when it occurs. The ultrasonic signal is characterized in that the appearance is almost periodical, and that the amplitude is nearly equal to each another. As described above, the ultrasonic signal generated by both in a metal wipe has certain characteristics in the generation period and signal amplitude. Accordingly, the metal wipe damages can be detected by monitoring such a ultrasonic signal.

In accordance with the above-mentioned objects of the invention, method and apparatus are disclosed for detecting the metal wipe of plane bearings, wherein the method includes the steps of receiving ultrasonic signal by a transducer fixed in the neighborhood of the plane bearings, and deciding whether the ultrasonic signal is generated periodically or not, and wherein the apparatus includes means fixed in the neighborhood of the plane bearings for receiving ultrasonic signal generated by the metal wipe, means for converting the received ultrasonic signal into a pulse signal, means for storing every pulse signal received within a predetermined period of time, and means for computing the ratio of the pulse signal stored within the previous period of time to that stored within the current period of time provided an output signal indicative of a metal wipe.

According to the present invention, an impending failure in the plane bearings of the rotary machine can be detected in an initial stage before the rubbing or the axial vibration occurs.

Other objects and advantages of the invention will become apparent from the following detailed description taken in connection with the accompanying drawings.

DESCRIPTION OF THE PREFERRED EMBODIMENTS

Figure 1:
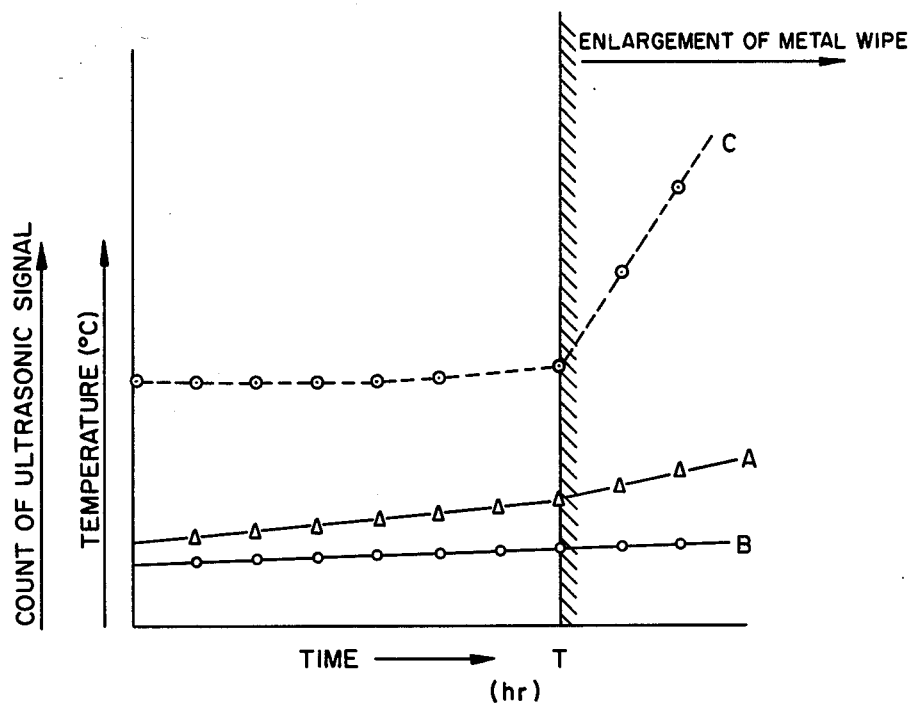
FIG. 1 is a graph showing the count of ultrasonic signal, the Babbit metal temperatures and the oil purging temperatures.

With reference to FIG. 1, Babbit metal temperatures are represented by a curve designated A, oil purging temperatures by a curve designated, B and ultrasonic are represented by a curve C, with the data in the graphical representation being obtained from experiments conducted to determine the metal wipe damages.

Figure 2:
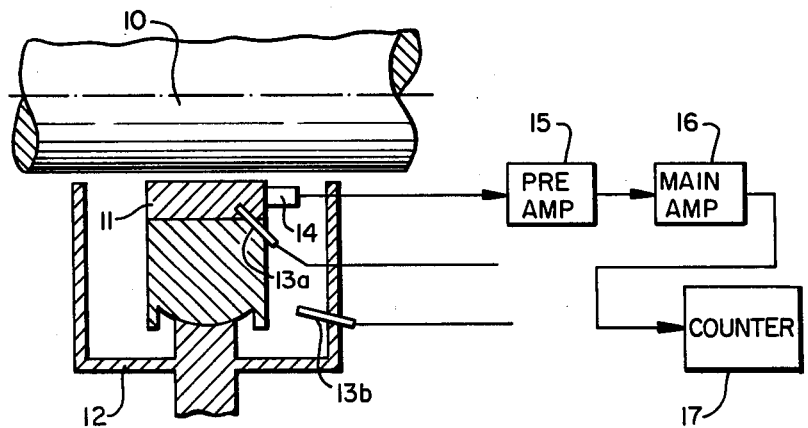
FIG. 2 is a diagram showing an arrangement of the detectors for receiving the ultrasonic signal, the Babbit metal temperature and the oil purging temperatures, and a circuit for processing the received ultrasonic signal.

Referring to FIG. 2, the Babbit metal temperatures A and the oil purging temperatures B, respectively, are measured by thermocouples 13a and 13b which are provided in Babbit metal 11 and housing 12, respectively. The ultrasonic signal is received by using a transducer 14 fixed to the Babbit metal 11. The received ultrasonic signal is amplified by a preamplifier 15 and a main amplifier 16, and is counted by a counter 17.

As shown in FIG. 1, the Babbit metal temperatures A and the oil purging temperatures B increase slowly before and after the occurrence of metal wipe (time T). However, the number of the ultrasonic signals increases significantly after a metal wipe has occurred.

Figure 3:
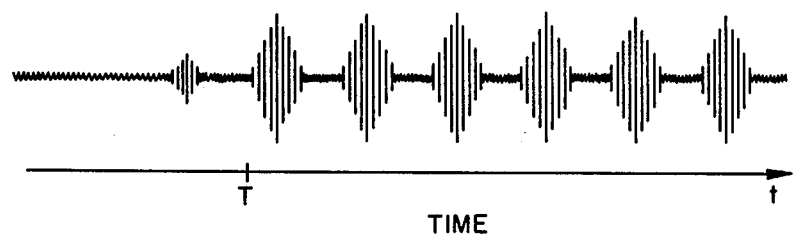
FIG. 3 is a wave form diagram depicting output ultrasonic signal generated by the metal wipe.

FIG. 3 illustrates a waveform of the ultrasonic signal generated by the metal wipe. In FIG. 3, the abscissa indicates time, in which T designates a time point of occurrence of the metal wipe. The ultrasonic signal occurs during about the same period, with an amplitude of the signal being about the same magnitude.

As described above, the ultrasonic signal generated by the metal wipe has certain characteristics both in a period of generation and the amplitude of the signal. Accordingly, the metal wipe can be detected by monitoring the ultrasonic signal.

Figure 4:
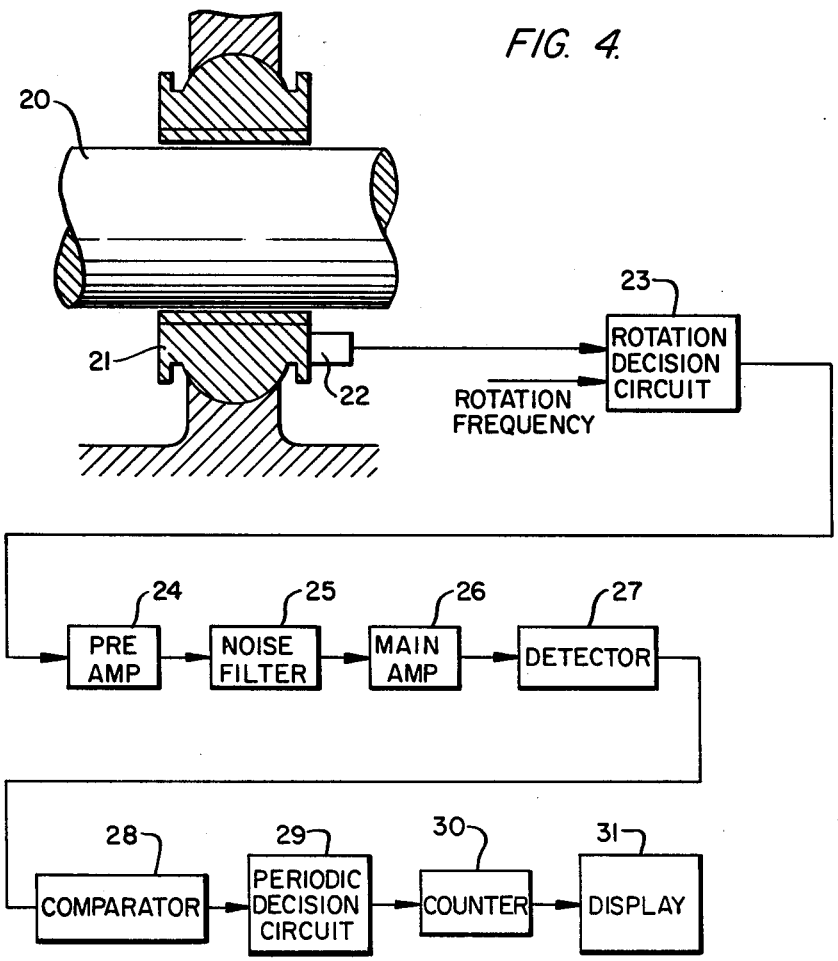
FIG. 4 is a block diagram of an illustrative embodiment of the present invention.

As shown in FIG. 4, a plane bearing arrangement is provided including a journal, 20 a plane bearing, 21 and a transducer 22 formed as a piezoelectric ceramic element. The transducer 22 is fixed by pressure welding or bonding at position where it can receive ultrasonic signal generated by the metal wipe damages on the surface of the plane bearing 21. The ultrasonic signal received by the transducer 22 is supplied to a rotation decision circuit 23 (the rotation operation is the preliminary operation of machine speed of about 2 rpm). A signal of a rotation frequency is also supplied to the circuit 23. The rotation decision circuit decides whether the machine is in the turning operation or in a normal operation, to supply an output signal of the transducer 22 to a preamplifier 24 only when the machine is in a rotation operation. If it is obvious that the machine is in a rotation operation, the output signal of the transducer 22 can be applied directly to the preamplifier 24. The preamplified signal is supplied through a noise filter 25 to a main amplifier 26. The amplified signal is supplied through a detector 27 to a comparator 28. The comparator 28 converts the ultrasonic signal into pulse signal. The pulse signal is supplied to a periodic decision circuit 29, in which the periodic nature of the pulse signal is detected. The output signal of the eriodic decision circuit 29 is applied to a counter 30 when the periodic nature is detected, that is, the output signal, hereinafter referred to as a metal wipe signal, of the circuit 29 indicates the occurrence of the metal wipe. The count of the output signal is displayed on a display 31.

Figure 5:
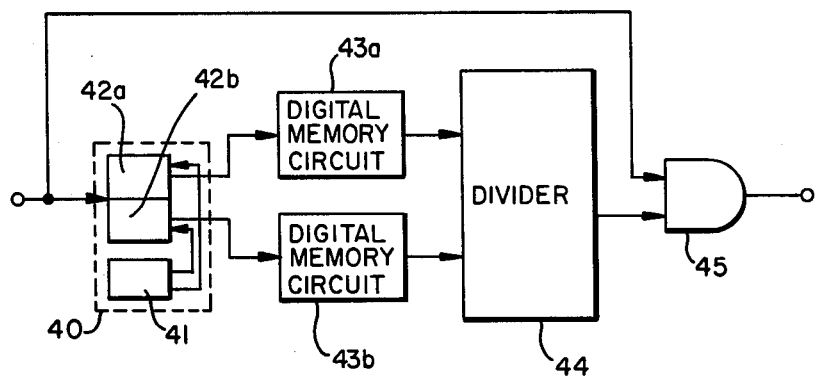
FIG. 5 is a block diagram of the periodic decision circuit shown in FIG. 4.
Figure 6:
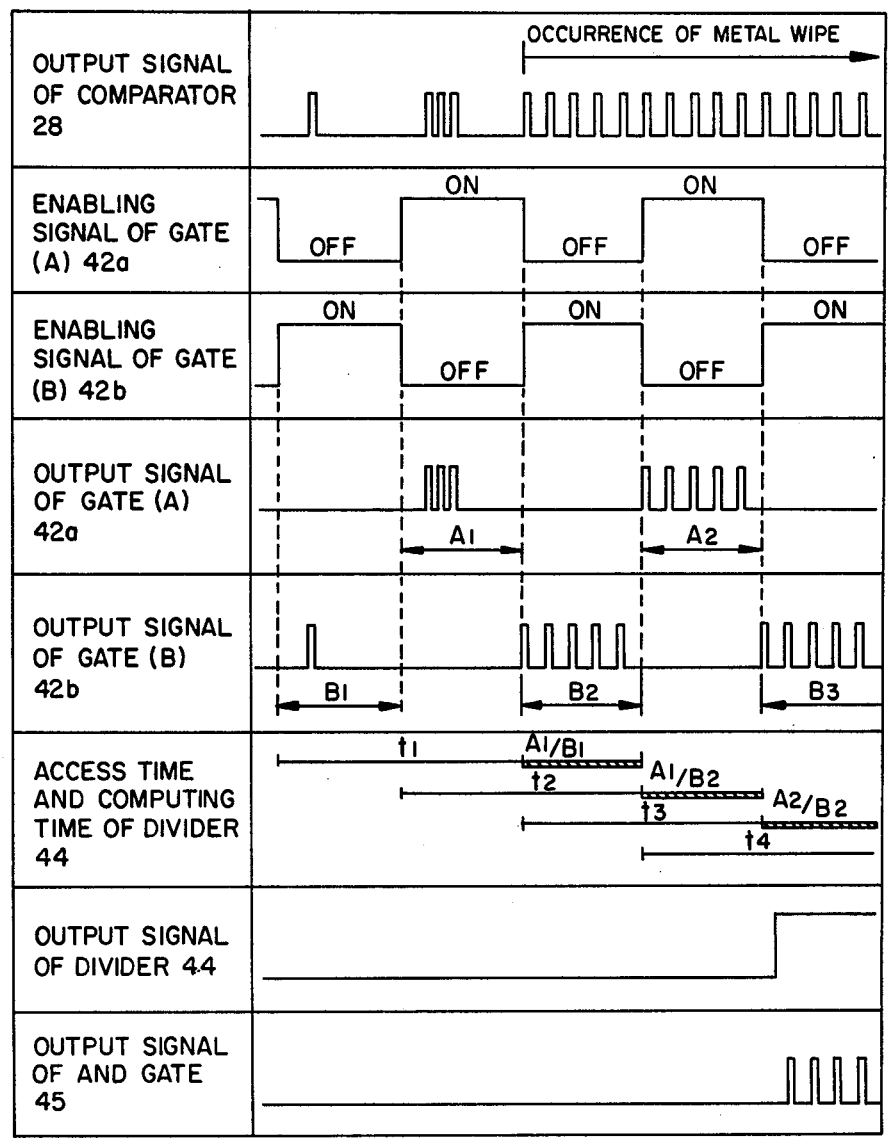
FIG. 6 is a wave form diagram depicting various signals developed at several points in FIG. 5.

FIG. 5 shows the periodic decision circuit shown in FIG. 4, with FIG. 6 illustrating waveforms of various signals developed at several points in FIG. 5.

Referring to FIG. 5 and FIG. 6, the output signal of the comparator 28 is applied to a gate circuit 40, which includes a timer 41. A gate (A) 42a and a gate (B) 42b are operated alternately by the timer 41 so as to pass the output signal to digital memory circuits 43a and 43b, respectively. The digital memory circuits are constructed such that the stored signal is cleared upon an input of a next signal.

As described above the ultrasonic signal is generated periodically after the metal wipe occurred. Therefore, the occurrence of the metal wipe can be detected by computing in the following manner.

The signals stored in the digital memory circuits 43a and 43b are applied to a divider 44 every read-in time $t_1$, $t_2$, $t_3$, - - - . The ratio of the output signal A of the circuit 43a to the output signal B of the circuit 43b, that is, $A_1/B_1$, $A_1/B_2$, $A_2/B_2$, etc. is computed by the divider 44. The divider 44 outputs a direct voltage signal as 5 volts when the signal A nearly equals to the signal B. Finally, an AND gate 45 performs an AND logical operation in response to the application of the output signal of the comparator 28 and that of the divider 44.

The foregoing operation is clearly illustrated by the waveforms of FIG. 6, wherein a heavy lines designates computation time. The divider 44 reads in the signals $A_2$ and $B_2$ within a period of time $t_3$, and computes $A_2/B_2$ within the next period of time $t_4$ to output the direct voltage signal which acts as a gate signal of the AND gate 45.

Figure 7:
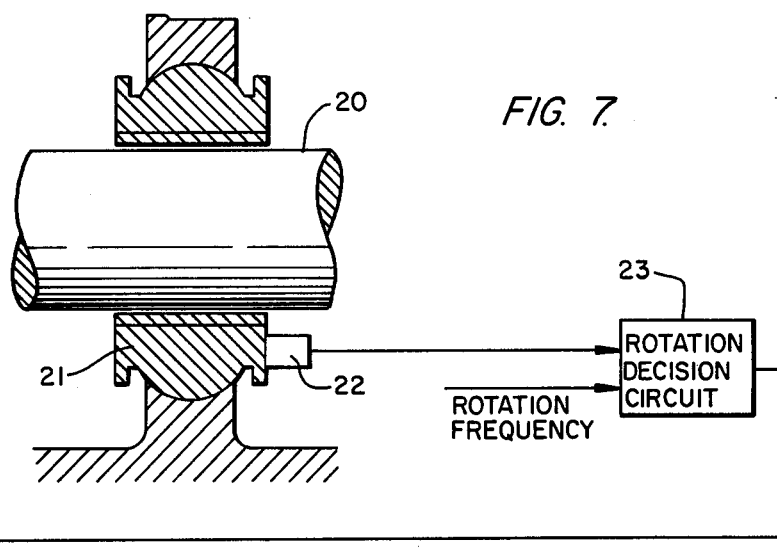
FIG. 7 is a block diagram of another embodiment of the present invention.
Figure 7:
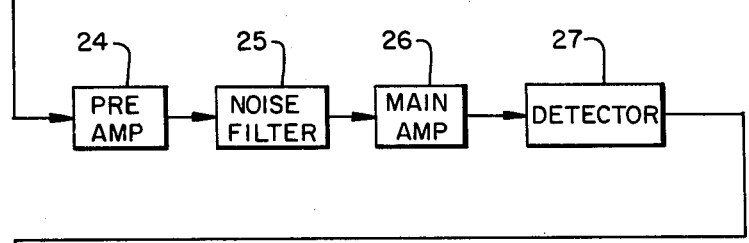
Figure 7:
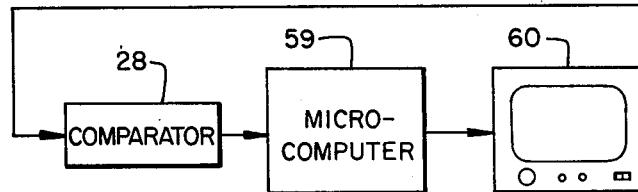

FIG. 7 shows another embodiment of the present invention, wherein a microcomputer 59 and a CRT display 60 are provided. In this embodiment, the microcomputer 59 is employed instead of the periodic decision circuit 29 and the counter 30 shown in FIG. 4 however, the apparatus functions in a similar manner to the apparatus of FIG. 4.

What is claimed is:

1. An apparatus for detecting a metal wipe of plane bearing means, the apparatus comprising means disposed in an area of the plane bearing means for receiving an ultrasonic signal generated by the metal wipe and for producing an output signal thereof, means for receiving the output signal and for converting the same into a pulse signal, means for receiving and storing the pulse signals received over a predetermined period of time, means for computing a ratio of a stored pulse signal with a previously predetermined period of time to a currently stored pulse signal and for providing an output signal indicative of an occurrence of the metal wipe, said means for computing a ratio includes a gate circuit means for receiving a pulse signal from said means for receiving and converting, means for operating the gate circuit means so as to provide for alternate output signals to said means for receiving and storing the pulse signals, divider means for receiving an output signal from said means for receiving and storing the pulse signals and for providing a divided output signal, and means responsive to the output signal of the means for receiving and converting and the divider means for providing the output signal indicative of the occurrence of a metal wipe.

2. An apparatus according to claim 1, wherein said gate circuit means includes at least two individual gates.

3. An apparatus according to claim 2, wherein said means for receiving and storing the pulse signals includes at least two digital memory circuit means respectively receiving output signals from said individual gates.

4. An apparatus according to claim 3, wherein each of said memory circuit means is adapted to clear a stored signal upon an input of a subsequent output signal from the respective gates.

5. An apparatus according to claim 3, wherein said means for operating the gate circuit means includes a timer means.

6. An apparatus according to claim 5, wherein said means responsive to the output signal of the receiving means includes an AND gate.

7. An apparatus according to claim 6, wherein said means for receiving and converting includes a comparator.

8. An apparatus according to claim 1, further comprising means interposed between said means for receiving the ultrasonic signal and said means for receiving and converting for determining whether the apparatus is in a preliminary turning operation or a normal operation.

9. An apparatus according to claim 8, wherein said means for determining includes a rotation decision circuit means for receiving a rotation frequency signal and the output signal from said means for receiving an ultrasonic signal.

10. An apparatus according to claim 9, further comprising a first amplifier means receiving an output signal from said rotation decision circuit means, a filter means for receiving an output signal from said first amplifier means, a second amplifier means for receiving an output signal from said filter means, and a detector means interposed between said second amplifier means and said means for receiving and converting.

11. An apparatus according to claim 10, further comprising a counter means for counting the output signal from said means for computing.

12. An apparatus according to claim 1, further comprising a display means for displaying the count of said counter means.

* * * * *